(12) United States Patent
Min et al.

(10) Patent No.: US 10,213,156 B2
(45) Date of Patent: Feb. 26, 2019

(54) HEADSET APPARATUS FOR DETECTING MULTI-BIOSIGNAL

(71) Applicant: SoSo Co., Ltd., Daegu (KR)

(72) Inventors: Dong-Bin Min, Gimpo-si (KR); Jae-Yong Lee, Seoul (KR); Dae-Sik Keum, Seoul (KR); Yoon-Ha Hwang, Daegu (KR); Won-Pyo Kim, Daegu (KR); Sang-Tak Kim, Daegu (KR); Yoo-Jin Jung, Daegu (KR)

(73) Assignee: SoSo Co. Ltd., Daegu (KR)

( * ) Notice: Subject to any disclaimer, the term of this patent is extended or adjusted under 35 U.S.C. 154(b) by 457 days.

(21) Appl. No.: 14/843,140

(22) Filed: Sep. 2, 2015

(65) Prior Publication Data
US 2016/0262704 A1 Sep. 15, 2016

(30) Foreign Application Priority Data
Mar. 12, 2015 (KR) .................. 10-2015-0034699

(51) Int. Cl.
| | |
|---|---|
| *A61B 5/04* | (2006.01) |
| *A61B 5/00* | (2006.01) |
| *A61B 5/0245* | (2006.01) |
| *A61B 5/0478* | (2006.01) |
| *A61B 5/0205* | (2006.01) |

(52) U.S. Cl.
CPC .......... *A61B 5/6803* (2013.01); *A61B 5/0245* (2013.01); *A61B 5/0478* (2013.01); *A61B 5/4884* (2013.01); *A61B 5/6816* (2013.01); *A61B 5/02055* (2013.01)

(58) Field of Classification Search
CPC ....... A61B 5/00; A61B 5/0456; A61B 5/0476; A61B 5/16; A61B 5/6803; A61B 5/0245; A61B 5/0478; A61B 5/4884; A61B 5/6816; A61B 5/02055
See application file for complete search history.

(56) References Cited

U.S. PATENT DOCUMENTS

| | | | |
|---|---|---|---|
| 6,293,904 B1 * | 9/2001 | Blazey | ..................... A61B 5/16 434/236 |
| 9,138,558 B1 * | 9/2015 | Kusik | .................... A61B 5/486 |

(Continued)

*Primary Examiner* — Navin Natnithithadha
*Assistant Examiner* — Eric J Messersmith
(74) *Attorney, Agent, or Firm* — NSIP Law

(57) ABSTRACT

The invention relates to a headset apparatus for detecting a multi bio-signal comprising: a headset body configured to be mounted on a user's head; a plurality of electrodes which are exposed on an outer surface of the headset body so as to be in contact with a forehead of a user when the headset body is mounted on a user's head; a brainwave detection unit which is embedded in the headset body and which detects a brainwave signal based on a signal detected by the plurality of electrodes; a heartbeat detection module which extends from the headset body through a signal cable and which is configured to be mounted on a user's ear to detect a heartbeat signal; and a headset controller to determine a complex stress index based on the brainwave signal detected by the brainwave detection unit and the heartbeat signal detected by the heartbeat detection module. Accordingly, the apparatus can measure a user's stress index accurately by measuring a multi bio-signal such as a brainwave and can be manufactured in the form of a wearable device.

8 Claims, 5 Drawing Sheets

(56) References Cited

U.S. PATENT DOCUMENTS

| | | | |
|---|---|---|---|
| 9,538,949 B2* | 1/2017 | Al-Ali | |
| 9,814,426 B2* | 11/2017 | Connor | A61B 5/6814 |
| 2010/0217103 A1* | 8/2010 | Abdul-Hafiz | A61B 5/14552 |
| | | | 600/322 |
| 2016/0220163 A1* | 8/2016 | Yamada | G06F 19/3481 |
| 2017/0319122 A1* | 11/2017 | Wild | A61B 5/165 |

* cited by examiner

HEADSET APPARATUS FOR DETECTING MULTI-BIOSIGNAL

CROSS-REFERENCE TO RELATED APPLICATIONS

This application claims the benefit under 35 USC 119(a) of Korean Patent Application No. 10-2015-0034699, filed on Mar. 12, 2015, in the Korean Intellectual Property Office, the entire disclosure of which is incorporated herein by reference for all purposes.

TECHNICAL FIELD

The present invention relates to a headset apparatus for detecting a multi bio-signal and in particular to a headset apparatus for detecting a multi bio-signal which can measure a user's stress index more accurately by measuring a multi bio-signal such as a user's brainwave and a heartbeat and which can be provided in the form of a wearable device.

BACKGROUND ART

Human's brain is the most flexible and highly adaptable regarding sensitivity, perception, thinking, behavior, etc. Human's brain consists of hundreds of billions of nerve cells and each nerve cell is connected with other nerve cells to form various interactions, which is called Synapse. The interaction is the key to the human's mental activity such as study, memory, recognition, activity, decision, etc. and is responsible for a human's physical control function to maintain health. Synapse is formed by a chemical reaction and the chemical reaction is converted into a scalp's electric flow to form a brainwave. That is, hundreds of billions of nerve cells send information with an interaction with other nerve cells and during this process, an electric signal is generated. Therefore, if an electrode is put into the scalp to measure electrical changes, the electrical changes are expressed as a wave. This wave is a brainwave (electroencephalogram; EEG).

The brainwave has various shapes depending on the degree of the brain activity. The frequency of the brainwave increases as the brain activity is high and the frequency of the brainwave decreases as the brain activity is low. The brainwave is divided into a gamma wave, a beta wave, an alpha wave, a theta wave and a delta wave.

A gamma wave is the fastest wave with a frequency between 38 to 45 Hz and with a mean frequency of 40 Hz and is generated when a human is nervous or in an active and highly complex mental process.

A beta wave is a wave with a frequency between 15 to 38 Hz and with a mean frequency of 17.3 Hz and is generated in a cerebrum during an active brain process. Further, a beta wave is generated when a human is nervous or suffers from stress. In particular, a high-beta wave is generated during an excessive activity, e.g., when a human suffers from an obsession, an excessive concentration and an anxiety.

An alpha wave is a wave with a frequency between 8 to 12 Hz and with a mean frequency of 10.3 Hz and is generated in an occipital lobe in a awakened state which is not a an unconscious state or a subconscious state with eyes closed. An alpha wave is mainly generated in a stress-relaxation state and is often generated before or after a severe stress.

A theta wave is a wave with a frequency between 4 to 8 Hz and with a mean frequency of 6.3 Hz and is generated dominantly in a pleocortex which mainly relates to emotion or sensitivity. Since a theta wave mainly relates to an area of emotion or sensitivity, it is generated considerably when a human makes an artistic effort, gets hurt, is happy, is working cheerfully or is playing.

A delta wave is a wave with a frequency between 0.5 to 4 Hz and with a mean frequency of 1.3 Hz and has the largest amplitude such that it has a strong penetration force to move furthest. A delta wave is generated mainly in a myelencephalon, a pons or a mesencephalon which relates to life and is generated mainly when a human is in deep sleep which stops activities in a paleocortex area relating to emotion and a neocortex area relating to information input/output and thought.

Meanwhile, a research on a new brainwave called SMR (Sensory Motor Rhythm) between a beta wave and an alpha wave is being carried out actively. A SMR wave is a wave between 12 to 15 Hz and with a mean frequency of 12.7 Hz. A SMR wave is generated dominantly in a cerebrum (neocortex) from an ear to a brain.

A SMR wave is generated when a problem requiring a simple concentration is being solved or when a relaxation is needed in a conscious state. That is, a SMR wave is generated when a human can concentrate on an easy and simple work accurately without nervousness or stress. A SMR wave turned out to be a brainwave generated in a concentrated state in that a SMR wave allows all matters to be solved with a very small amount of energy compared to beta wave.

Using measurement values of the brainwaves as above, a human's state such as a mentality or a mental condition can be expressed with an index. In one example, as shown in Formula 1 below, it is being suggested how a concentration index, a relaxation index, a stress index, etc. can be calculated by each of the above explained waves which consist the brainwave.

concentration index=(SMR wave+$M$ beta wave)/theta wave relaxation index=alpha wave/$H$ beta wave stress index=high beta wave　　　　　　　　　　[Formula 1]

Regarding a technology using the above brainwave, a method to measure a degree of a user's stress through brainwaves and use the measurements is being suggested. In one example, Korean laid-open publication No. 10-2007-0061311 titled "Recognition of stress state by brainwave and relaxation system and method using music" discloses a technique to remove stress by acquiring a stress state more reliably using characteristic information which is obtained from the brainwave during analyzing a brainwave to understand the degree of stress and by playing music which is set depending on the acquired stress state.

However, in prior arts including the technique disclosed in Korean laid-open publication No. 10-2007-0061311, only one brainwave feature, e.g., a magnitude of a high-beta wave, is being used to measure a user's brainwave. It is disadvantageously incorrect to evaluate a user's stress index only by a brainwave since a user's stress characteristic is generated in the form of various bio-signals.

On the other hand, to evaluate a stress index based on various bio-signals, an apparatus for detecting more than two bio-signals should be mounted on a human. While a wearable device is becoming known recently, it is not easy to design an apparatus for detecting more than two bio-signals as a wearable device. Therefore, it is not easy for a user to measure a stress index accurately in a daily life and to reflect it on the life.

DISCLOSURE OF THE INVENTION

Technical Problem

The invention is provided to solve the above problem. The purpose of the invention is to measure a user's stress index accurately by measuring a multi bio-signal such as a brainwave and a heartbeat and to provide a headset apparatus for detecting a multi bio-signal which can be manufactured in the form of a wearable device.

Technical Solution

The above purpose can be achieved by a headset apparatus for detecting a multi bio-signal comprising: a headset body configured to be mounted on a user's head; a plurality of electrodes which are exposed on an outer surface of the headset body so as to be in contact with a forehead of a user when the headset body is mounted on a user's head; a brainwave detection unit which is embedded in the headset body and which detects a brainwave signal based on a signal detected by the plurality of electrodes; a heartbeat detection module which extends from the headset body through a signal cable and which is configured to be mounted on a user's ear to detect a heartbeat signal; and a headset controller to determine a complex stress index based on the brainwave signal detected by the brainwave detection unit and the heartbeat signal detected by the heartbeat detection module.

Here, the headset controller is configured to analyze frequencies of the brainwave signal to extract an alpha wave and a high-beta wave and to calculate a brainwave stress index based on the alpha wave and the high-beta wave; to calculate a heartbeat stress index based on the variation of a R-peak interval of the heartbeat signal; and to apply a predetermined weight factor to the brainwave stress index and the heartbeat stress index, respectively and add them up to calculate a complex stress index.

Also, the headset controller is configured to divide the brainwave stress index into 10 levels and divide the heartbeat stress index into 5 levels, and the headset controller is configured to divide a complex stress index into 10 levels by calculating the complex stress index using the following formula:

$$SI = ROUND(((n \times SI\_B) + (m \times SI\_H))/2, 1)$$

wherein SI is a complex stress index, SI_B is a brainwave stress index, SI_H is a heartbeat stress index, n is a weight factor for the brainwave stress index, m is a weight factor for the heartbeat stress index, and a function of ROUND( ) is a round-off function to raise decimals to the next whole number.

Also, the headset controller is configured to divide the brainwave stress index into 10 levels by calculating the brainwave stress index by the following formula:

$$SI\_B = ROUND((\alpha/\beta) \times 10, 1)$$

wherein $\alpha$ is a magnitude of an alpha wave and $\beta$ is a magnitude of a high-beta wave.

Further, the headset controller is configured to measure a R-peak interval from the heartbeat signal for a predetermined time; to calculate a Full width at half maximum (FWHM) of a histogram of the R-peak interval; and to calculate the heartbeat stress index by normalizing the FWHM to a value ranging from 0 to 1, by multiplying the normalized value by 5 and then by omitting decimals, such that the heartbeat stress index is divided into 5 levels.

Also, the headset apparatus further comprises a headset wireless communication unit embedded in the headset body to carry out a wireless communication, wherein the headset controller is configured to send the complex stress index to an external device through the headset wireless communication unit.

Also, the headset apparatus further comprises a headset wireless communication unit embedded in the headset body to carry out a wireless communication, wherein the headset controller comprises a headset control module embedded in the headset body to send the brainwave signal and the heartbeat signal to an external device through the headset wireless communication unit and a stress measuring program installed on the external device to measure a complex stress index based on the brainwave signal and the heartbeat signal which are sent to the external device through the headset wireless communication unit.

Here, the heartbeat detection module is configured in the form of clamps to be mounted on a user's ear.

Also, the headset apparatus further comprises a permanent magnet which is provided on one of an outer surface of the heartbeat detection module and an outer surface of the headset body; and a magnetic substance which is provided on the other of an outer surface of the heartbeat detection module and an outer surface of the headset body and which has magnetic material or magnetizable material, wherein the heartbeat detection module are configured to be attached to and detached from the headset body by the attachment of the permanent magnet and the magnetic substance.

Advantageous Effect

According to the invention, a headset apparatus for detecting a multi bio-signal is provided which can measure a user's stress index accurately by measuring a multi bio-signal such as a brainwave and which can be manufactured in the form of a wearable device.

Also, it is possible to simplify the arrangement of a headset body by dividing a headset controller into a control module and a stress measurement program such that a weight and a size of the headset body is reduced and in turn it is possible to reduce the manufacturing cost by the simplification of a hardware.

Further, the invention can be configured to receive only the actually-measured brainwave signal and heartbeat signal from the headset body. Therefore, it is possible to use a brainwave and a heartbeat for other use by installing other application programs besides the stress measurement program on an external device, thereby expanding the use of the headset apparatus for detecting a multi bio-signal according to the invention.

DETAILED DESCRIPTION

Hereinafter, embodiments of the present invention will be explained in detail referring to attached drawings.

Figure 3:
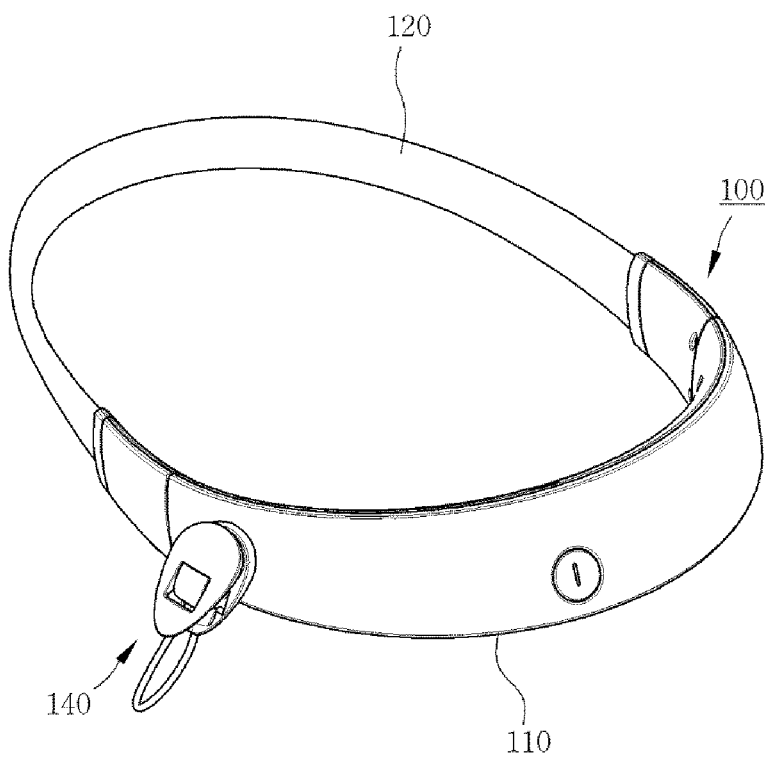
Figure 4:
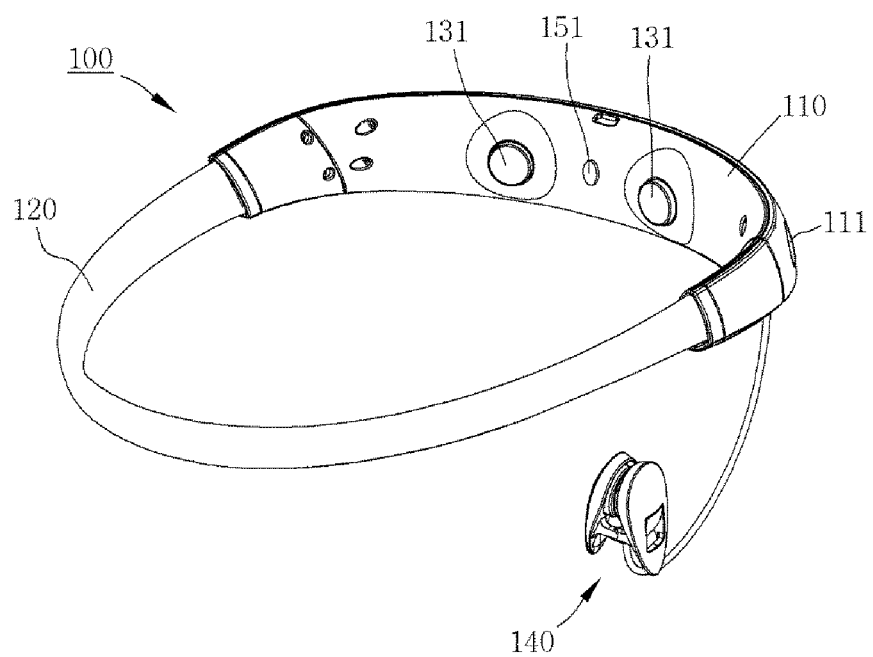
Figure 5:
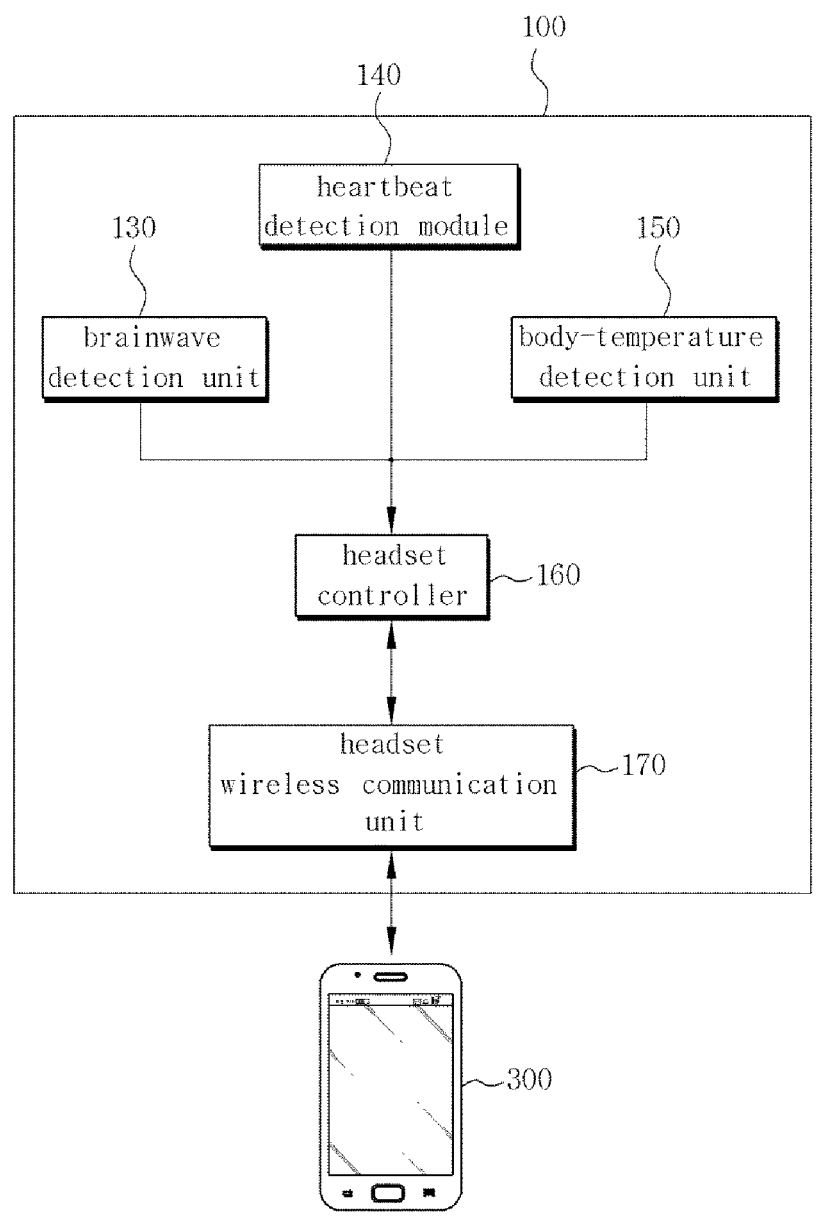
FIG. 5 is a control block diagram of a headset apparatus for detecting multi bio-signal according to the present invention.

FIGS. 1 to 4 represent a headset apparatus 100 for detecting a multi bio-signal according to the invention and FIG. 5 shows a control block diagram of the headset apparatus for detecting multi bio-signal according to the invention.

Referring to FIGS. 1 to 5, the headset apparatus 100 for detecting a multi bio-signal according to the present invention comprises a headset body 110, 120, a plurality of electrodes 131, a brainwave detection unit 130, a heartbeat detection module 140 and a headset controller 160.

The headset body 110, 120 is configured to be mounted on a user's head. In one example as shown in FIGS. 1 to 4, the headset body 110, 120 is arranged in the form of a headband, but the shape of the headset body is not limited to this.

Further, the headset body 110, 120 comprises a body module 110 in which a circuit arrangement such as the brainwave detection unit 130 or the heartbeat detection unit 140 is embedded and an elastic headset band 120 which is connected to the body module 110. With this arrangement, the elasticity of the headset band 120 allows the headset body 110, 120 to be mounted on the user's head stably regardless of the size of the user's head.

The plurality of electrodes 131 are exposed on the surface of the body module 110 of the headset body 110, 120 such that they are in contact with a user's forehead when the headset body 110, 120 is mounted on the user's head. In an embodiment of the present invention, as shown in FIG. 4, a pair of electrodes 131 is provided, but the number of the electrode is not limited to this.

The brainwave detection unit 130 is embedded in the body module 110 of the headset body 110, 120 such that the brainwave can be determined based on a signal detected by a plurality of electrodes 131.

Figure 1:
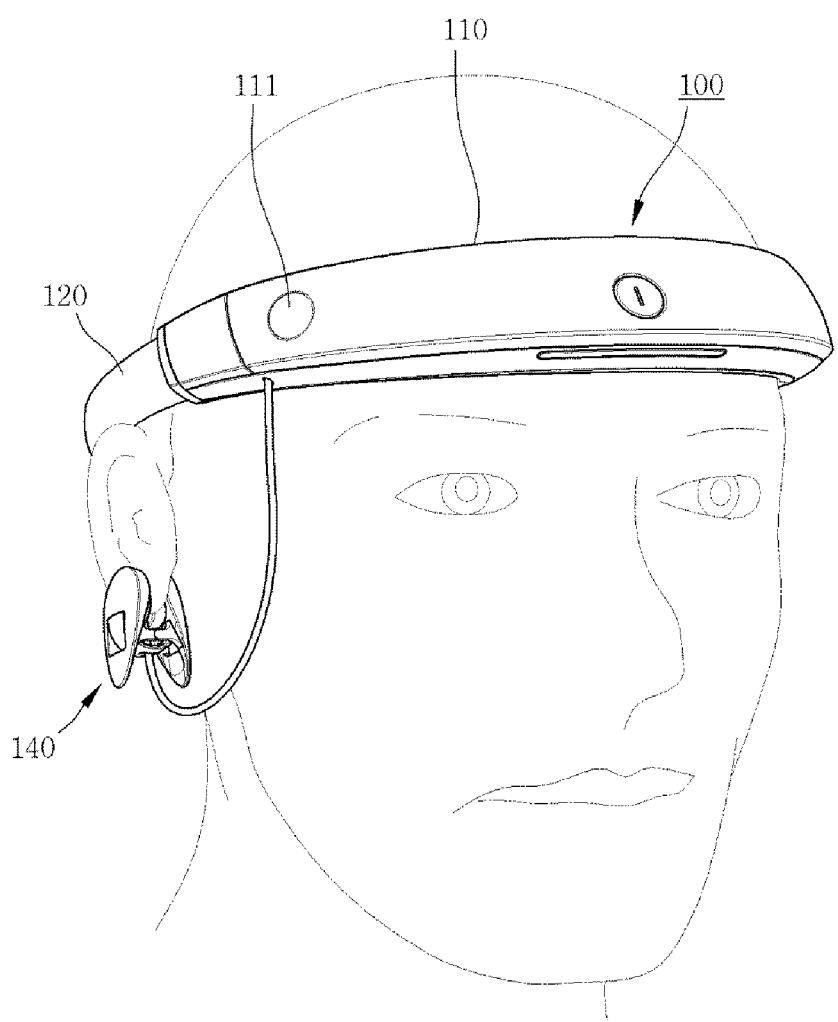
FIGS. 1 to 4 represent an arrangement of a headset apparatus for detecting multi bio-signal according to the present invention.
Figure 2:
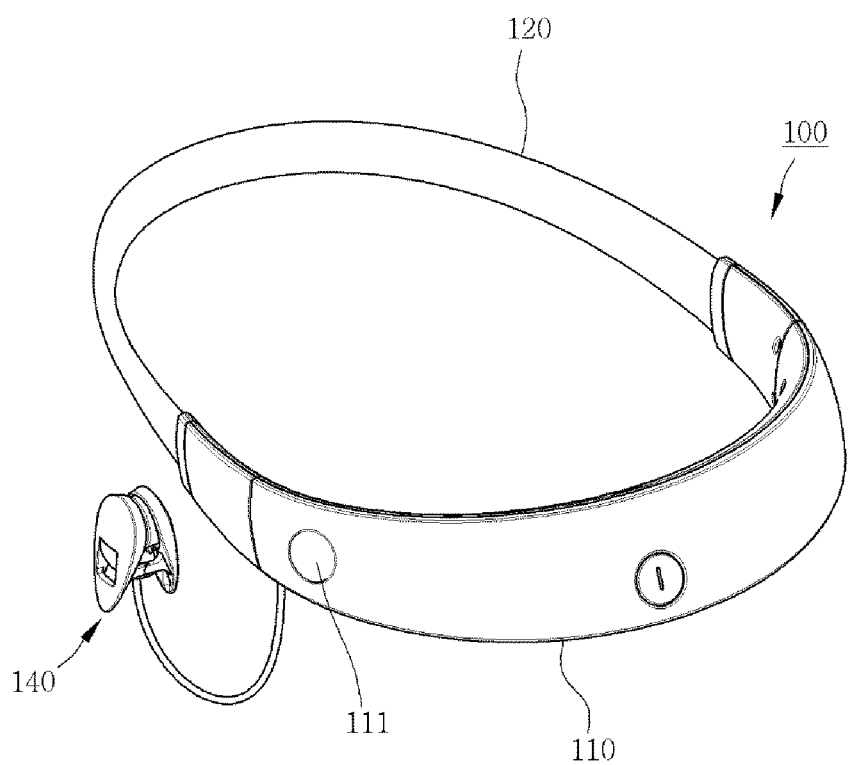

The heartbeat detection module 140 extends from the headset body 110, 120 by a signal cable and as shown in FIG. 1, it is configured to be mounted on an earlobe so as to detect a user's heartbeat signal.

Herein, the heartbeat detection module 140 is configured in the form of clamps to be mounted on the user's earlobe. As shown in FIG. 1, a user wears the headset apparatus 100 for detecting a multi bio-signal according to the invention and mounts the heartbeat detection module 140 which extends through a signal cable on the earlobe, such that a wearable device which detects a brainwave and a heartbeat simultaneously is realized.

Further, a permanent magnet 111 is mounted on the body module 110 of the headset body 110, 120 and a magnetic substance (not shown) is provided to the heartbeat detection module 140. Here, the magnetic substance can be a magnetic material such as a magnet or a magnetizable material such as a metal. Therefore, as shown in FIG. 3, when a user keeps and stores the headset apparatus 100 for detecting a multi bio-signal according to the invention, he attaches the magnetic substance of the heartbeat detection module 140 to the permanent magnet 111 of the headset substance 110, 120 in order to keep the apparatus. Here, it is understood that the permanent magnet 111 can be mounted on the heartbeat detection module 140 and the magnetic substance can be provided to the body module 110 of the headset body 110, 120.

Meanwhile, the controller determines a user's complex stress index based on a brainwave signal detected by the brainwave detection unit 130 and a heartbeat signal detected by the heartbeat detection module 140.

Here, the headset controller 160 analyzes frequencies of the brainwave to extract an alpha wave and a high-beta wave and calculates a brainwave stress index based on the alpha wave and the high-beta wave. Also, the headset controller 160 calculates a heartbeat stress index based on the variation of a R-peak interval of the heartbeat signal.

Hereinafter, it will be explained in detail how the headset controller 160 according to the invention calculates a brainwave stress index, a heartbeat stress index and a complex stress index.

The headset controller 160 may divide the brainwave stress index into 10 levels. In more detail, the headset controller 160 can calculate the brainwave stress index by Formula 1 below.

$$SI\_B = ROUND((\alpha/\beta) \times 10, 1)$$ [Formula 1]

In Formula 1, α is a magnitude of an alpha wave, β is a magnitude of a high-beta wave, and SI_B is a brainwave stress index. A function of ROUND( ) is a round-off function to round off to the first decimal place. Using this function, the final brainwave stress index can be calculated as a fixed number ranging from 1 to 10 such that the brainwave stress index can be divided into 10 levels. Then, the headset controller 160 measures a R-peak interval from the heartbeat signal for a predetermined time, e.g., two minutes and calculates a full width at half maximum (FWHM) of a histogram of the R-peak interval.

Then, the headset controller 160 normalizes FWHM to a value ranging from 0 to 1, multiplies the normalized value by 5 and then omits decimals such that the heartbeat stress index is calculated. Therefore, the heartbeat stress index can be divided into five levels.

Using the brainwave stress index and the heartbeat stress index calculated in the above example, the headset controller 160 can calculate a complex stress index by Formula 2 below.

$$SI = ROUND(((n \times SI\_B) + (m \times SI\_H))/2, 1)$$ [Formula 2]

In Formula 2, SI is a complex stress index, SI_B is a brainwave stress index, SI_H is a heartbeat stress index, n is a weight factor to the brainwave stress index and m is a weight factor to the heartbeat stress index.

A function of ROUND( ) a round-off function to raise decimals to the next whole number and using this function, a complex stress index is calculated to be divided into 10 levels.

By the above method, the headset controller 160 applies a predetermined weight factor to the brainwave stress index and the heartbeat stress index, respectively and then add them to calculate a complex stress index, so as to determine a user's stress index which comprehensively reflects the variation of the brainwave and the heartbeat from bio-signals.

As shown in FIG. 5, the headset apparatus 100 for detecting a multi bio-signal comprises a headset wireless communication unit 170. The headset wireless communication unit 170 is embedded in the body module 110 of the headset body 110, 120 to carry out a wireless communication. In one example, the headset wireless communication unit 170 is configured to carry out telecommunication through a WIFI network based on TCP/IP or a Bluetooth.

The headset controller 160 is configured to send a complex stress index to an external device 300, such as a smart phone as shown in FIG. 5, through the headset wireless communication unit 170 such that a user can see a stress index by the smartphone or various contents can be provided according to the stress index.

In the above embodiment, the headset controller 160 embedded in the headset body 110, 120 sends a calculated complex stress index to the external device 300 by means of the headset wireless communication unit 170. In other embodiments, the headset controller 160 can be configured such that a headset control module (not shown) is embedded in the headset body 110, 120 and a stress measuring program (not shown) is installed on the external device 300.

In more detail, the headset module embedded in the headset body 110, 120 can send a brainwave signal detected by the brainwave detection unit 130 and a heartbeat signal detected by the heartbeat detection module 140, to the external device 300 such as a smart phone by means of the headset wireless communication unit 170.

Further, the stress measurement program is installed on the external device 300 and is operable based on an operating system of the external device 300. As explained in the above embodiment, using the brainwave signal and the heartbeat signal sent to the external device 300 by means of the headset wireless communication unit 170, the brainwave stress index and the heartbeat stress index are calculated and then a complex stress index can be calculated with the two indexes.

The simplification of the headset body 110, 120 reduces the weight and size of the headset body 110, 120 and also reduces the production cost.

Also, the invention is configured such that only the brainwave signal and the heartbeat signal measured by the headset body 110, 120 are sent and other application programs besides the stress measurement program are installed on the external device 300 so that the brainwave and the heartbeat can be used for other purposes, thereby the use of the headset apparatus 100 for detecting a multi bio-signal according to the invention can be expanded.

In one example, as shown in FIGS. 4 and 5, a body-temperature detection unit 150 for measuring a body-temperature and a body-temperature detection terminal 151 are installed on the headset body 110, 120 and the headset controller 160 sends the user's temperature measured by the body-temperature detection unit 150 and the body-temperature detection terminal 151 to the external device 300 so that the invention is applicable to various use such as checking a current body-temperature of a user.

It will be appreciated that the above embodiments are intended to describe some of the technical spirit which is comprised in the invention and various modifications or specific embodiments which can be expected by those skilled in the art within the scope of the invention comprised in the specification may be comprised within the spirit of the invention.

| List of reference numeral | |
|---|---|
| 100: headset apparatus for detecting multi bio-signal | |
| 110: body module | 111: permanent magnet |
| 120: headset band | 130: brainwave detection unit |
| 131: electrode | 140: heartbeat detection module |
| 150: body-temperature detection unit | 151: body-temperature detection terminal |
| 160: headset controller | 170: headset wireless communication unit |
| 300: external device | |

The invention claimed is:

1. A headset apparatus for detecting a multi bio-signal, comprising:
    a headset body configured to be mounted on a head of a user;
    a plurality of electrodes which are exposed on an outer surface of the headset body so as to be in contact with a forehead of the user when the headset body is mounted on the head of the user;
    a brainwave detection sensor embedded in the headset body, and configured to detect a brainwave signal based on a signal detected by the plurality of electrodes;
    a heartbeat detection sensor extending from the headset body through a signal cable, and configured to be mounted on an ear of the user to detect a heartbeat signal; and
    a headset controller configured to
        analyze frequencies of the brainwave signal to extract an alpha wave and a beta wave,
        calculate a brainwave stress index based on the alpha wave and the beta wave,
        calculate a heartbeat stress index based on a variation of an R-peak interval of the heartbeat signal,
        respectively apply predetermined weight factors to the brainwave stress index and the heartbeat stress index to generate a weighted brainwave stress index and a weighted heartbeat stress index, and
        add the weighted brainwave stress index and the weighted heartbeat stress index to calculate a complex stress index.

2. The headset apparatus according to claim 1, wherein the headset controller is further configured to divide the brainwave stress index into ten levels and divide the heartbeat stress index into five levels, and the headset controller is further configured to divide a complex stress index into ten levels by calculating the complex stress index using the following formula:

$$SI=ROUND(((n \times SI\_B)+(m \times SI\_H))/2,1)$$

wherein SI is a complex stress index, SI_B is the brainwave stress index, SI_H is the heartbeat stress index, n is a weight factor among the weight factors for the brainwave stress index, m is a weight factor among the weight factors for the heartbeat stress index, and ROUND( ) is a round-off function to raise decimals to a next whole number.

3. The headset apparatus according to claim 2, wherein the headset controller is further configured to divide the brainwave stress index into the ten levels by calculating the brainwave stress index by the following formula:

$$SI\_B=ROUND((\alpha/\beta) \times 10,1)$$

wherein $\alpha$ is a magnitude of the alpha wave and $\beta$ is a magnitude of the beta wave.

4. The headset apparatus according to claim 2, wherein the headset controller is further configured to measure the R-peak interval from the heartbeat signal for a predetermined time, to calculate a Full Width at Half Maximum (FWHM) of a histogram of the R-peak interval, and to calculate the heartbeat stress index by normalizing the FWHM to a value ranging from 0 to 1, by multiplying the normalized value by 5 and then by omitting decimals, such that the heartbeat stress index is divided into five levels.

5. The headset apparatus according to claim 2, further comprising a headset transceiver embedded in the headset body, wherein the headset controller is further configured to send the complex stress index to an external device through the headset transceiver.

6. The headset apparatus according to claim 2, further comprising a headset transceiver embedded in the headset body, wherein the headset controller comprises a headset control module embedded in the headset body to send the brainwave signal and the heartbeat signal to an external device through the headset transceiver and a stress measuring program installed on the external device to measure the complex stress index based on the brainwave signal and the heartbeat signal.

7. The headset apparatus according to claim 1, wherein the heartbeat detection sensor comprises a clamp configured to be mounted on the ear of the user.

8. The headset apparatus according to claim 1, further comprising:
   a permanent magnet disposed on either one of an outer surface of the heartbeat detection sensor and an outer surface of the headset body; and
   a magnetic material disposed on the other of the outer surface of the heartbeat detection sensor and the outer surface of the headset body,
   wherein the heartbeat detection sensor is configured to be detachably coupled to the headset body by the permanent magnet and the magnetic substance.

* * * * *